United States Patent [19]
Reid et al.

[11] Patent Number: 5,591,583
[45] Date of Patent: Jan. 7, 1997

[54] HUMAN RESTRICTIN AND NUCLEIC ACID SEQUENCES

[75] Inventors: Robert A. Reid, Durham; Rhonda L. Ackley, Chapel Hill; John J. Hemperly, Apex, all of N.C.

[73] Assignee: Becton, Dickinson and Company, Franklin Lakes, N.J.

[21] Appl. No.: 404,665

[22] Filed: Mar. 15, 1995

[51] Int. Cl.$^6$ .............................. C12Q 1/68; C12N 1/20; C12N 15/00; C07H 21/04
[52] U.S. Cl. .................. 435/6; 435/252.3; 435/320.1; 536/23.5
[58] Field of Search .................. 435/6, 252.3, 320.1; 536/23.5

[56] References Cited

PUBLICATIONS

L. Vaughan, et al. "Tenascin–Contactin/F11 Interactions: A Clue for A Developmental Role?" *Persp. Dev. Neurobiol.* 2:43–52 (1994).

M. Schachner, et al. "The Perplexiing Multifunctionality of Janusin, a Tenascin–Related Molecule" *Perp. Dev. Neurobiol.* 2:33–41 (1994).

R. Chiquet–Ehrismann, et al. "The Tenascin Gene Family" *Perp. Dev. Neurobiol.* 2:3–7 (1994).

F. G. Rathjen, et al. "Restrictin: a chick neural extracellular matrix protein involved in cell attachment co–purifies with the cell recognition molecule F11" *Development* 113:151–164 (1991).

A. Lochter, et al. "The Extracellular Matrix Molecule Janusin Regulates Neuronal Morphology in a Substrate–and Culture Time–dependent Manner" *Euro. J. Neurosci.* 6:597–606 (1994).

P. Pesheva, et al. "Tenascin–R (J1 160/180) inhibits fibronectin–mediated cell adhesion –functional relatedness to tenascin–C" *J. Cell Sci.* 107:2323–2333 (1994).

Bristow et al. (1993) J. Cell Biol. 122(1): 265–278.

*Primary Examiner*—Robert A. Wax
*Assistant Examiner*—Lisa J. Hobbs
*Attorney, Agent, or Firm*—Donna R. Fugit

[57] ABSTRACT

Human restrictin proteins and nucleic acid sequences encoding them are provided. Antibodies which recognize human restrictin in human brain are disclosed. In the human brain, restrictin occurs as two major polypeptides of 180 and 160 kD located in fiber tracts. These polypeptides are similar to those seen in rat brain. Surprisingly, restrictin has also been found in the peripheral nerves of rats and humans. The antibodies also detect a 170 kD polypeptide in MATRIGEL, an extracellular matrix product of rat EHS sarcoma cells widely used as a tissue culture substrate. Monoclonal antibodies to human restrictin and assays using the human restrictin protein, antibodies and DNA sequences are also provided.

5 Claims, 1 Drawing Sheet

HUMAN RESTRICTIN AND NUCLEIC ACID SEQUENCES

FIELD OF THE INVENTION

The present invention relates to extracellular matrix molecules and nucleic acid sequences encoding them.

BACKGROUND OF THE INVENTION

The adherence of cells to each other and to the extracellular matrix, as well as the cellular signals transduced as a consequence of such binding, are of fundamental importance to the development and maintenance of body form and function. A number of molecules mediating cell adhesion have been identified and characterized at the molecular level both in vertebrates and in invertebrates. Many cell surface cell adhesion molecules (CAMs) are of three major types: 1) members of the immunoglobulin supergene family, which mediate calcium independent adhesion, 2) cadherins, which mediate calcium-dependent adhesion and are important structural components of adherence junctions, and 3) integrins, a family of heterodimeric proteins which can facilitate adhesion of cells both to each other and to the extracellular matrix.

CAMs may have multiple ligands. They can mediate adhesion by the interaction of a CAM on one cell with the identical CAM on another cell (homophilic binding), or they can mediate adhesion by interacting with different CAMs or extracellular matrix molecules (heterophilic binding). For example, contactin, a member of the immunoglobulin gene superfamily, can undergo homophilic binding or can bind heterophilically to other cell surface molecules such as the L1 antigen or to extracellular matrix molecules of the tenascin family. One extracellular matrix ligand for contactin is janusin, which is a member of the tenascin-R family. Janusin is closely related to tenascin in its patterns of epidermal growth factor, fibronectin type III and fibrinogen-like domains. In rodents, it is synthesized by oligodendrocytes and subpopulations of neurons at late developmental stages in the central nervous system. It can promote cell adhesion or anti-adhesion, depending on the neural cell type with which it interacts, promoting neurite outgrowth of some neural cell types and inhibiting neurite outgrowth from other neuronal populations. The repulsive response of neurons to janusin may be mediated by contactin. Janusin has been identified in rodents (A. Faissner, et al. 1990. Neurochem. 54:1004–1015) and the rat gene has been cloned (B. Fuss, et al. 1991. J. Neurosci. Res. 29:299–307) and sequenced (B. Fuss, et al. 1993. J. Cell Biol. 120:1237–1249). The chicken homolog of janusin, referred to as restrictin, has also been identified and characterized (U. Norenberg, et al. 1992. Neuron 8:849–863).

SUMMARY OF THE INVENTION

Prior to the present invention, no human homolog of janusin/restrictin had been identified and it was not previously known if such a homolog existed. A human homolog of rat janusin has now been found, and the complete cDNA sequence encoding it has been determined. Antisera were prepared against a fragment of the human restrictin protein expressed in bacteria. These antibodies detect the immunogen, high molecular weight polypeptides in human brain, and cross react with several animal species. In the human brain, restrictin occurs as two major polypeptides of 180 and 160 kD located in fiber tracts. These polypeptides are similar in size to those seen in rat brain. Surprisingly, restrictin has also been found in the peripheral nerves of rats and humans. The antibodies also detect a 170 kD polypeptide in MATRIGEL, an extracellular matrix product of rat EHS sarcoma cells widely used as a tissue culture substrate. Monoclonal antibodies to human restrictin and assays using the human restrictin protein, antibodies and DNA sequences are also provided.

DETAILED DESCRIPTION OF THE INVENTION cDNAs encoding human restrictin were cloned from human brain polyA+ RNA using the reverse transcriptase polymerase chain reaction (RT-PCR) with primers based on the rat janusin gene sequence. RT-PCR was performed on rat and human (adult and fetal, Clontech) brain polyA+ RNA using the one-step protocol described by Goblet, et al. (1989. Nucl. Acids Res. 17:2144). PolyA+ RNA (1 µg) and 300 ng of each primer (see below) in 66 µl DEPC water were incubated at 65° C. for 15 min. and cooled on ice. Thirty-three µl of 3× RT-PCR reagent mix (3× PCR buffer, 150 mM KCl, 30 mM Tris-HCl pH 8.3, 4.5 mM MgCl$_2$, 0.3% gelatin, 500 µM dNTPs, 200 U M-MLV reverse transcriptase, 4 U rRNAsin (Promega, Madison, Wis.), 2.5 U AMPLITAQ (Perkin-Elmer Cetus, Norwalk, Conn.) was added and the reaction was incubated at 37° C. for 30 min. The amplification reaction (94° C. for 1 min., 50° C. for 2 min., and 72° C. for 2 min.) was repeated for 40 cycles. The primer pair for amplification was as follows:

| | |
|---|---|
| 5'-ACTGACAGATCTAGAGCC | SEQ ID NO:1 (corresponding to nucleotides 2375–2392 in rat) |
| 5'-GGTGGTCGATAGGATACT | SEQ ID NO:2 (corresponding to nucleotides 2856–2839 in rat) |

A major 480 bp amplification product was obtained from rat RNA, which was subcloned and sequenced, confirming that this product corresponded to rat janusin. A minor 290 bp product was also obtained in rat. An amplification product of the appropriate size (480 bp) was also generated from human adult brain RNA. This product was subcloned and sequenced directly (Mihovilovic, 1989). Amplification of fetal RNA produced only a 290 bp amplification product which was subsequently found not to be human restrictin.

The 480 bp human amplification product (206/207N) was used as a probe on Northern blots of multiple regions of human brain (Clontech). The radiolabeled probe was prepared using a random primer labeling kit (BRL, Gaithersburg, Md.) with purification over NICK columns (Pharmacia, Piscataway, N.J.). Blots were reprobed with a human beta-actin probe (Clontech) to determine the relative amounts and integrity of RNA in each sample. The probe hybridized to a single approximately 12 Kb nucleic acid sequence in amygdala, caudate nucleus, corpus collusum, hippocampus, hypothalamus, substantia nigra, subthalamic nuclei and thalamus. The restrictin cDNA clones described below were also used as probes on northern blots of human fetal tissues. The approximately 12 Kb restrictin mRNA seen in adult brain was also detected in fetal brain, but was absent from fetal heart, lung, liver and kidney. This illustrates the tissue specificity of restrictin.

Figure 1:
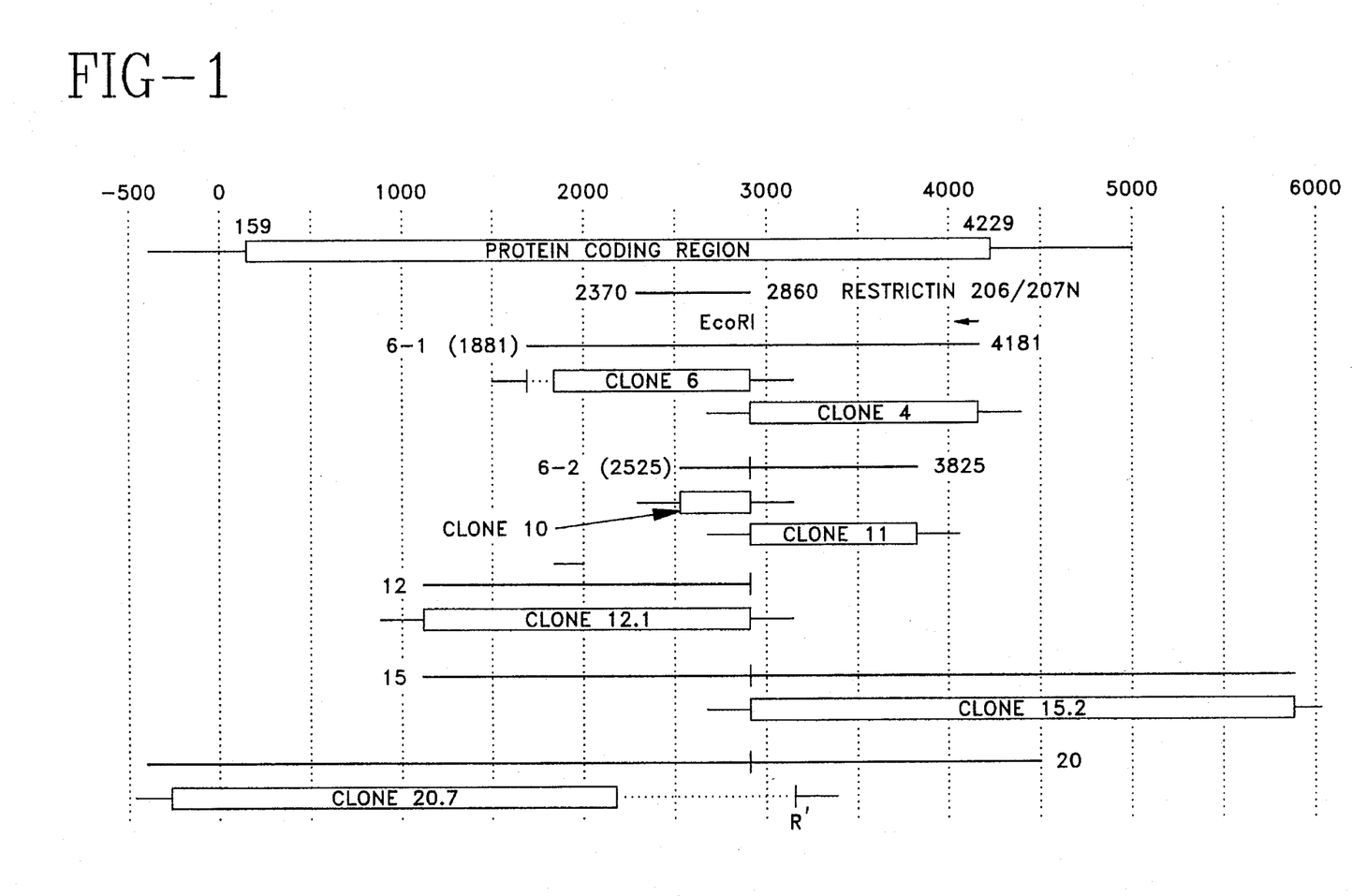
FIG. 1 illustrates the cloning process used to obtain the human restrictin cDNA sequence.

Two commercially available lambda human cDNA libraries were screened as recommended by the manufacturer using 206/207N as a probe to identify additional clones for determination of the sequence of the full-length human restrictin gene (FIG. 1). Initial screening with 206/207N identified cDNA clones 6-1 and 6-2. A second hybridization screening using a probe from the 5' end of clone 6-1, as illustrated in FIG. 1, produced cDNA clones 12 and 15. The upstream end of clone 12 was used in a third library screen to isolate clone 20. Together, these clones encode the entire protein coding region of human restrictin (FIG. 1). The lambda cDNA inserts of these clones were either 1) PCR amplified using lambda gt10 EcoRI forward and reverse primers for direct sequencing as described above (Mihovilovic, 1989), or 2) subcloned into pBLUESCRIPT (SK+) (Stratagene, La Jolla, Calif.) for sequencing by dye-termination or dye-labeled primer methods (Applied Biosystems, Model 373A, Foster City, Calif.). Sequencing primers were synthesized on an Applied Biosystems (ABI) Model 380B DNA synthesizer and purified using OPC cartridges (ABI). Sequence alignments, translations, and feature location were performed using IG-Suite software (Intelligenetics, Mountain View, Calif.). In this manner, the entire 4,724 bp human restrictin cDNA coding sequence was determined by sequencing both strands of the cDNAs (SEQ ID NO:3). The sequence of the full-length restrictin protein (1358 amino acids, SEQ ID NO:4) was deduced from the cDNA sequence. The human restrictin protein shows structural similarity to other members of the tenascin-R family. In particular, human restrictin, like its homologs from rat and chicken, comprises a short amino terminal region followed by heptad repeats, epidermal growth factor-like repeats, nine fibronectin type III repeats and a carboxyl-terminal region homologous to the globular domain of fibrinogen. There is no evidence for a hydrophobic membrane spanning region, consistent with restrictin being a secreted, extracellular matrix molecule. The human sequence obtained is highly homologous to the rat and chicken sequences at both the DNA (88 and 76%, respectively, within the protein coding region) and at the amino acid level (93 and 72%, respectively).

SEQ ID NO:3, a fragment of SEQ ID NO:3, or an equivalent nucleic acid molecule which employs degenerate codons to encode the amino acid sequence of SEQ ID NO:4 or a fragment thereof, may be cloned into an expression vector as is known in the art to produce recombinant human restrictin in transformed or transfected host cells. Recombinant human restrictin and recombinant human restrictin fragments provide a convenient source of these molecules for immunization, immunoassays, and use in tissue culture growth substrates. To generate antisera to human restrictin, the 206/207N fragment (nucleotides 2686–3165 of SEQ ID NO:3 with EcoRI cloning sites at both the 5' and 3' ends) was subcloned into the EcoRI site of pGEX-3X (Pharmacia), producing a recombinant human restrictin-glutathione-S-transferase (GST) fusion protein for immunization. After transformation of *E. coli*, expression of the fusion protein was induced with IPTG and the soluble material was purified over a glutathione-S Sepharose affinity column. The purified material was used to immunize rabbits using standard methods. Sera were collected and assayed by immunoblotting against the immunogen and against the 206/207N protein fragment, expressed by subcloning into the pATH expression system (New England BioLabs). The anti-fusion protein antisera recognized both of these antigens on Western blots, but anti-chicken restrictin did not, indicating immunological differences between the human and chicken restrictin proteins.

To verify the reactivity of the antisera against human proteins, adult brain membranes were prepared and extracted. In brief, postmortem human brain was Dounce homogenized into 0.32 M sucrose, 5 mM EDTA, 20 mM Tris-HCl (pH 8) containing 1 mM PMSF, 0.5 mM p-chloromercuriphenylsulfonic acid and 5 µg/ml of aprotinin and leupeptin as protease inhibitors. After centrifugation at 500×g for 30 min. to remove nuclei and cellular debris, the supernatant was centrifuged at 80,000×g to collect the membrane fraction, which was then extracted with 1% sodium deoxycholate in homogenization buffer for 1.5 hr. at 4° C. The detergent extract was clarified by centrifugation at 100,000×g and used subsequently for either SDS-PAGE directly or for further purification of a protein fraction bearing the HNK-1 epitope, which may be involved in binding cell adhesion molecules. HNK-1 brain fractions were immunoaffinity enriched on anti-Leu7 (Becton Dickinson) coupled to Sepharose. Immunoblotting was performed using a PROTOBLOT AP system (Promega) as recommended by the manufacturer with an alkaline phosphatase-conjugated anti-rabbit IgG as the secondary antibody and color development using NBT/BCIP. In Western blots, the anti-fusion protein antisera routinely detected two bands of approximately 180 and 160 kD in human brain and in HNK-1 enriched fractions. These bands were apparently enriched in the latter. The reactivity of the antisera was inhibited in a concentration dependent manner by addition of the GST fusion protein, but not by addition of GST, indicating a specific immune reaction to the human restrictin fragment. Western blots of rat, mouse, cow, pig and chicken brain extracts demonstrated similar sized bands (180 kD and 160 kD) in all cases. There were, however, slight mobility shifts, possibly due to species variation in amino acid sequence or to differential glycosylation. MATRIGEL (Collaborative Biomedical Products), an extracellular matrix substrate derived from rat EHS sarcoma cells as an in vitro tissue culture growth substrate, was also reactive with the antiserum, revealing a 170 kD polypeptide.

For immunohistological studies, frozen human or rat tissues were sectioned and fixed using acetone or 4% paraformaldehyde. Staining was performed using the VECTA-STAIN ELITE ABC system (Vector Laboratories) as recommended. Primary anti-fusion protein antisera were used at a 1:1000 dilution. Paraffin sections were treated using the microwave antigen retrieval system (U.S. Pat. No. 5,244,787) before staining. The antisera were reactive with frozen sections of human peripheral nerve (peripheral nervous system), rat hippocampus (central nervous system) and human cerebellum (central nervous system) and with paraffin section human pons (central nervous system). In all cases, there were areas of clear positivity as well as areas that were clearly negative. For example, in the peripheral nerve experiments, the surrounding, non-neuronal tissue was unstained, and in the central nervous system, there were clearly unstained cells in all areas examined.

Antibodies according to the invention which recognize human restrictin are useful in methods for detecting the protein in immunoassay systems. Polyclonal antisera raised to human restrictin or to protein fragment of human restrictin may be used to detect the restrictin protein in immunoassay methods involving binding between the protein or fragment and the antibodies, e.g., ELISAs and immunoblots. These conventional immunoassay methods can be readily adapted to employ the antibodies and restrictin protein disclosed herein. Alternatively, monoclonal antibodies which recognize the human restrictin protein of the invention may be prepared using methods known in the art, such as that of Kohler and Milstein (1975. *Nature* 256:495) and used in immunoassays. The spleen cells of mice immunized with the human restrictin protein or a fragment thereof are fused with murine myeloma cells and the resulting hybridomas are screened against the immunogen to select those producing the desired anti-restrictin monoclonal antibody. In general, binding between protein and antibody in an immunoassay is detected by inclusion of a detectable label in the reaction which generates a signal. The detectable label is usually conjugated to the antibody or protein and may be directly detectable (e.g., a dye, radioisotope or fluorochrome) or rendered detectable after further chemical reaction (e.g., an enzyme which reacts to produce a colored product, or biotin which may be bound to labeled avidin).

Polyclonal and monoclonal antibodies according to the invention may also be used to purify human restrictin from tissues, or to purify restrictin from the tissues of a cross-reacting species by immunoaffinity purification methods, e.g., immunoaffinity chromatography. This provides a source of natural restrictin for use in immunoassays, as an immunogen, or in tissue culture systems to promote or inhibit neurite outgrowth.

Oligonucleotides derived from the nucleotide sequences encoding human restrictin are useful in nucleic acid hybridization assays for detection of related restrictin nucleotide sequences. They may also be used as primers for amplification of restrictin target sequences. Oligonucleotide probes for hybridization according to the invention may comprise the complete coding sequence of the human restrictin cDNA or a portion thereof, such as nucleotides 2686–3165 of SEQ ID NO:3. Primers are generally short portions of the nucleotide sequence which specifically hybridize to restrictin nucleotide sequences, allowing specific amplification. One skilled in the art will further recognize that oligonucleotide probes and primers may also be designed which comprise all or a portion of a sequence which is complementary to SEQ ID NO:3. Detection of nucleic acids by hybridization to a probe is known in the art. Such methods as Southern blotting, Northern blotting, dot blotting, nucleic acid amplification methods and the like may be readily adapted to detection of nucleotide sequences containing all or part of the human restrictin coding sequence, or to detection of all or part of the restrictin coding sequence of a cross-reacting species. This is done using the nucleotide sequence given in SEQ ID NO:3 to design appropriate probes and primers. For purposes of the present invention, the terms "encoding" and "coding for" are intended to include nucleic acids which comprise sequences which can be transcribed and/or translated to produce restrictin, or a fragment thereof, including degenerate nucleotide sequences. It will also be understood that probes and primers derived from the disclosed nucleotide sequences may also be used to detect fragments of restrictin coding sequences. Hybridization of the probe or amplification by the primers may be detected by means of a directly or indirectly detectable label associated with the probe or primer, i.e., incorporated into the probe or conjugated to it. In general, the same labels useful for labeling antibodies and antigens may be used to label oligonucleotides. In addition, it is within the ordinary skill in the art, given the nucleotide sequence of SEQ ID NO:3, to derive the complementary nucleotide sequence, which may also be used to prepare probes and primers and which may be detected by use of probes and primers. Further, the present disclosure of SEQ ID NO:3 allows derivation of RNA sequences which are complementary to SEQ ID NO:3 or to the complement of SEQ ID NO:3. Such equivalent RNA sequences may be detected by hybridization or amplification as well.

The reagents for performing these immunoassays, hybridization assays, and nucleic acid amplification may be conveniently packaged together for sale or use in the form of a kit. A kit for immunoassay may contain an antibody which recognizes and binds to restrictin. The antibody may be labeled, or a second antibody carrying the label may be included for detection of binding. Optionally, any reagent required for performing the assay and detecting the label may be included. A kit for hybridization assays or amplification may contain oligonucleotide probes or primers which hybridize to one or more nucleotide sequences contained in SEQ ID NO:3. The probes or primers may be conjugated to a detectable label for detection. Optionally, the hybridization or amplification kit may contain any reagents required for performing the hybridization or amplification and detecting the label.

The foregoing disclosure is intended to illustrate the invention and is not to be construed as limiting its scope as defined by the appended claims. Upon reading the present disclosure, certain equivalents and variations will be apparent to one skilled in the art without exercise of inventive skill. Such equivalents and variations are intended to be included within the scope of the invention.

What is claimed is:

1. A nucleic acid molecule consisting of a nucleotide sequence selected from the group consisting of SEQ ID NO:3, a complement of SEQ ID NO:3, a degenerate nucleotide sequence which encodes SEQ ID NO:4, and RNA equivalents thereof.

2. A nucleic acid molecule consisting of a nucleotide sequence selected from the group consisting of nucleotides 2686–3165 of SEQ ID NO:3, a complement of nucleotides 2686–3165 of SEQ ID NO:3, and RNA equivalents thereof.

3. An expression vector comprising the nucleotide sequence of SEQ ID NO:3 or nucleotides 2686–3165 of SEQ ID NO:3.

4. A host cell transformed or transfected with the expression vector of claim 3.

5. A method for detecting a nucleic acid sequence encoding human restrictin comprising detecting hybridization of a nucleic acid molecule selected from the group consisting of SEQ ID NO:3, nucleotides 2686–3165 of SEQ ID NO:3 and complements thereof to the nucleic acid sequence.

* * * * *

SEQUENCE LISTING ( 1 ) GENERAL INFORMATION:

( i i i ) NUMBER OF SEQUENCES: 4

( 2 ) INFORMATION FOR SEQ ID NO:1:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear     ( x i ) SEQUENCE DESCRIPTION: SEQ ID NO:1:

ACTGACAGAT CTAGAGCC                                                                              1 8

( 2 ) INFORMATION FOR SEQ ID NO:2:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear     ( x i ) SEQUENCE DESCRIPTION: SEQ ID NO:2:

GGTGGTCGAT AGGATACT                                                                                     1 8

( 2 ) INFORMATION FOR SEQ ID NO:3:

( i ) SEQUENCE CHARACTERISTICS:
        ( A ) LENGTH: 4724 base pairs
        ( B ) TYPE: nucleic acid
        ( C ) STRANDEDNESS: double
        ( D ) TOPOLOGY: linear     ( i i ) MOLECULE TYPE: cDNA     ( x i ) SEQUENCE DESCRIPTION: SEQ ID NO:3:

```
GAATTCCGGG AGAAGGGGT  CCTCTCTGAC CCAAGGAATT ACCACTAGTG GAGTGAAGCC      60
ACCTGACTTT TTGATCTTAT TTTGGTTGCC TCCTCATTCT CCTTCCACCC GTAGCCCTGA     120
CAGCTTGGGT TTCATTTCTT TCGTGGAGCC TTGTCTCTTC CTCCCAGAAT AGGAGGAAGG     180
GAAGAGAAGG GAAAGAGGAG GGCTCTCTAG GTGAGCGCAT CAGCTGGCTC CAGCCTGAGC     240
AAGCAAGAAT TTCTTCCCA  GGAAGCTCCT CTCGCTCCCC GGCCGCCCAC CCCCAGCCTG     300
GGTGGCTGTA TCGTTTTAAC TGCATAGAGG GCAGGTCTCT TTTGGAATTA GGATTAAAGA     360
AAGTGCAGTA AAGAGAAAGC ATCGAAGACA CCATCACAAA AGATTCCCAC AACTCCATGC     420
TGTGTGCTGC AGGCTGGTCC TGAACCCAGA TCTCTGGCTG AGAGGATGGG GGCAGATGGG     480
GAAACAGTGG TTCTGAAGAA CATGCTCATT GGCGTCAACC TGATCCTTCT GGGCTCCATG     540
ATCAAGCCTT CAGAGTGTCA GCTGGAGGTC ACCACAGAAA GGGTCCAGAG ACAGTCAGTG     600
GAGGAGGAGG GAGGCATTGC CAACTACAAC ACGTCCAGCA AAGAGCAGCC TGTGGTCTTC     660
AACCACGTGT ACAACATTAA CGTGCCCTTG GACAACCTCT GCTCCTCAGG GCTAGAGGCC     720
TCTGCTGAGC AGGAGGTGAG TGCAGAAGAC GAGACTCTGG CAGAGTACAT GGGCCAGACC     780
TCAGACCACG AGAGCCAGGT CACCTTTACA CACAGGATCA ACTTCCCCAA AAAGGCCTGT     840
CCATGTTCCA GTTCAGCCCA GGTGCTGCAG GAGCTGCTGA GCCGGATCGA GATGCTGGAG     900
AGGGAGGTGT CGGTGCTGCG AGACCAGTGC AACGCCAACT GCTGCCAAGA AAGTGCTGCC     960
ACAGGACAAC TGGACTATAT CCCTCACTGC AGTGGCCACG GCAACTTTAG CTTTGAGTCC    1020
TGTGGCTGCA TCTGCAACGA AGGCTGGTTT GGCAAGAATT GCTCGGAGCC CTACTGCCCG    1080
CTGGGTTGCT CCAGCCGGGG GGTGTGTGTG GATGGCCAGT GCATCTGTGA CAGCGAGTAC    1140
AGCGGGGATG ACTGTTCCGA ACTCCGGTGC CCAACAGACT GCAGCTCCCG GGGGCTCTGC    1200
GTGGACGGGG AGTGTGTCTG TGAAGAGCCC TACACTGGCG AGGACTGCAG GGAACTGAGG    1260
TGCCCTGGGG ACTGTTCGGG GAAGGGAGA  TGTGCCACCG GTACCTGTTT ATGCGAGGAG    1320
GGCTACGTTG GTGAGGACTG CGGCCAGCGG CAGTGTCTGA ATGCCTGCAG TGGGCGAGGA    1380
CAATGTGAGG AGGGGCTCTG CGTCTGTGAA GAGGGCTACC AGGGCCCTGA CTGCTCAGCA    1440
GTTGCCCCTC CAGAGGACTT GCGAGTGGCT GGTATCAGCG ACAGGTCCAT TGAGCTGGAA    1500
TGGGACGGGC CGATGGCAGT GACGGAATAT GTGATCTCTT ACCAGCCGAC GGCCCTGGGG    1560
GGCCTCCAGC TCCAGCAGCG GGTGCCTGGA GATTGGAGTG GTGTCACCAT CACGGAGCTG    1620
```

```
GAGCCAGGTC TCACCTACAA CATCAGCGTC TACGCTGTCA TTAGCAACAT CCTCAGCCTT    1680
CCCATCACTG CCAAGGTGGC CACCCATCTC TCCACTCCTC AAGGGCTACA ATTTAAGACG    1740
ATCACAGAGA CCACCGTGGA GGTGCAGTGG GAGCCCTTCT CATTTTCCTT CGATGGGTGG    1800
GAAATCAGCT TCATTCCAAA GAACAATGAA GGGGGAGTGA TTGCTCAGGT CCCCAGCGAT    1860
GTTACGTCCT TTAACCAGAC AGGACTAAAG CCTGGGGAGG AATACATTGT CAATGTGGTG    1920
GCTCTGAAAG AACAGGCCCG CAGCCCCCT  ACCTCGGCCA GCGTCTCCAC AGTCATTGAC    1980
GGCCCCACGC AGATCCTGGT TCGCGATGTC TCGGACACTG TGGCTTTTGT GGAGTGGATT    2040
CCCCCTCGAG CCAAAGTCGA TTTCATTCTT TTGAAATATG GCCTGGTGGG CGGGGAAGGT    2100
GGGAGGACCA CCTTCCGGCT GCAGCCTCCC CTGAGCCAAT ACTCAGTGCA GGCCCTGCGG    2160
CCTGGCTCCC GATACGAGGT GTCAGTCAGT GCCGTCCGAG GGACCAACGA GAGCGATTCT    2220
GCCACCACTC AGTTCACAAC AGAGATCGAT GCCCCCAAGA ACTTGCGAGT TGGTTCTCGC    2280
ACAGCAACCA GCCTTGACCT CGAGTGGGAT AACAGTGAAG CCGAAGTTCA GGAGTACAAG    2340
GTTGTGTACA GCACCCTGGC GGGTGAGCAA TATCATGAGG TACTGGTCCC CAAGGGCATT    2400
GGTCCAACCA CCAGGGCCAC CCTGACAGAT CTGGTACCTG GCACTGAGTA TGGAGTTGGA    2460
ATATCTGCCG TCATGAACTC ACAGCAAAGC GTGCCAGCCA CCATGAATGC CAGGACTGAA    2520
CTTGACAGTC CCCGAGACCT CATGGTGACA GCCTCCTCAG AGACCTCCAT CTCCCTCATC    2580
TGGACCAAGG CCAGTGGCCC CATTGACCAC TACCGAATTA CCTTTACCCC ATCCTCTGGG    2640
ATTGCCTCAG AAGTCACCGT ACCCAAGGAC AGGACCTCAT ACACACTAAC AGATCTAGAG    2700
CCTGGGGCAG AGTACATCAT TTCCGTCACT GCTGAGAGGG GTCGGCAGCA GAGCTTGGAG    2760
TCCACTGTGG ATGCTTTCAC AGGCTTCCGT CCCATCTCTC ATCTGCACTT TTCTCATGTG    2820
ACCTCCTCCA GTGTGAACAT CACTTGGAGT GATCCATCTC CCCCAGCAGA CAGACTCATT    2880
CTTAACTACA GCCCCAGGGA TGAGGAGGAA GAGATGATGG AGGTCTCCCT GGATGCCACC    2940
AAGAGGCATG CTGTCCTGAT GGGCCTGCAA CCAGCCACAG AGTATATTGT GAACCTTGTG    3000
GCTGTCCATG GCACAGTGAC CTCTGAGCCC ATTGTGGGCT CCATCACCAC AGGAATTGAT    3060
CCCCCAAAAG ACATCACAAT TAGCAATGTG ACCAAGGACT CAGTGATGGT CTCCTGGAGC    3120
CCTCCTGTTG CATCTTTCGA TTACTACCGA GTATCATATC GACCCACCCA AGTGGGACGA    3180
CTAGACAGCT CAGTGGTGCC CAACACTGTG ACAGAATTCA CCATCACCAG ACTGAACCCA    3240
GCTACCGAAT ACGAAATCAG CCTCAACAGC GTGCGGGGCA GGGAGGAAAG CGAGCGCATC    3300
TGTACTCTTG TGCACACAGC CATGGACAAC CCTGTGGATC TGATTGCTAC CAATATCACT    3360
CCAACAGAAG CCCTGCTGCA GTGGAAGGCA CCAGTGGGTG AGGTGGAGAA CTACGTCATT    3420
GTTCTTACAC ACTTTGCAGT CGCTGGAGAG ACCATCCTTG TTGACGGAGT CAGTGAGGAA    3480
TTTCGGCTTG TTGACCTGCT TCCTAGCACC CACTATACTG CCACCATGTA TGCCACCAAT    3540
GGACCTCTCA CCAGTGGCAC CATCAGCACC AACTTTTCTA CTCTCCTGGA CCCTCCGGCA    3600
AACCTGACAG CCAGTGAAGT CACCAGACAA AGTGCCCTGA TCTCCTGGCA GCCTCCCAGG    3660
GCAGAGATTG AAAATTATGT CTTGACCTAC AAATCCACCG ACGGAAGCCG CAAGGAGCTG    3720
ATTGTGGATG CAGAAGACAC CTGGATTCGA CTGGAGGGCC TGTTGGAGAA CACAGACTAC    3780
ACGGTGCTCC TGCAGGCAAC ACAGGACACC ACGTGGAGCA GCATCACCTC CACCGCTTTC    3840
ACCACAGGAG GCCGGGTGTT CCCTCATCCC CAAGACTGTG CCCAGCATTT GATGAATGGA    3900
GACACTTTGA GTGGGGTTTA CCCCATCTTC CTCAATGGGG AGCTGAGCCA GAAATTACAA    3960
GTGTACTGTG ATATGACCAC CGACGGGGGC GGCTGGATTG TATTCCAGAG GCGGCAGAAT    4020
```

| | | | | |
|---|---|---|---|---|
| GGCCAAACTG | ATTTTTTCCG | GAAATGGGCT | GATTACCGTG | TTGGCTTCGG GAACGTGGAG | 4080 |
| GATGAGTTCT | GGCTGGGGCT | GGACAATATA | CACAGGATCA | CATCCCAGGG CCGCTATGAG | 4140 |
| CTGCGCGTGG | ACATGCGGGA | TGGCCAGGAG | GCCGCCTTCG | CCTCCTACGA CAGGTTCTCT | 4200 |
| GTCGAGGACA | GCAGAAACCT | GTACAAACTC | CGCATAGGAA | GCTACAACGG CACTGCGGGG | 4260 |
| GACTCCCTCA | GCTATCATCA | AGGACGCCCT | TTCTCCACAG | AGGATAGAGA CAATGATGTT | 4320 |
| GCAGTGACTA | ACTGTGCCAT | GTCGTACAAG | GGAGCATGGT | GGTATAAGAA CTGCCACCGG | 4380 |
| ACCAACCTCA | ATGGGAAGTA | CGGGGAGTCC | AGGCACAGTC | AGGGCATCAA CTGGTACCAT | 4440 |
| TGGAAAGGCC | ATGAGTTCTC | CATCCCCTTT | GTGGAAATGA | AGATGCGCCC CTACAACCAC | 4500 |
| CGTCTCATGG | CAGGGAGAAA | ACGGCAGTCC | TTACAGTTCT | GAGCAGTGGG CGGCTGCAAG | 4560 |
| CCAACCAATA | TTTTCTGTCA | TTTGTTTGTA | TTTTATAATA | TGAAACAAGG GGGGAGGGTA | 4620 |
| ATAGCAATGT | TTTTTGCAAC | ATATTAAGAG | TATGTNAAGG | AAGCAGGGAT GTCGCAGGAA | 4680 |
| TCCGCTGGCT | AACATCTGCT | CTNGGTTTCT | GCTGNCCTGG | AGGC | 4724 |

( 2 ) INFORMATION FOR SEQ ID NO:4:

( i ) SEQUENCE CHARACTERISTICS:
( A ) LENGTH: 1358 amino acids
( B ) TYPE: amino acid
( C ) STRANDEDNESS: single
( D ) TOPOLOGY: linear ( i i ) MOLECULE TYPE: protein ( x i ) SEQUENCE DESCRIPTION: SEQ ID NO:4:

```
Met Gly Ala Asp Gly Glu Thr Val Val Leu Lys Asn Met Leu Ile Gly
  1               5                  10                  15

Val Asn Leu Ile Leu Leu Gly Ser Met Ile Lys Pro Ser Glu Cys Gln
             20                  25                  30

Leu Glu Val Thr Thr Glu Arg Val Gln Arg Gln Ser Val Glu Glu Glu
         35                  40              45

Gly Gly Ile Ala Asn Tyr Asn Thr Ser Ser Lys Glu Gln Pro Val Val
     50                  55                  60

Phe Asn His Val Tyr Asn Ile Asn Val Pro Leu Asp Asn Leu Cys Ser
 65                  70                  75                  80

Ser Gly Leu Glu Ala Ser Ala Glu Gln Glu Val Ser Ala Glu Asp Glu
             85                  90                  95

Thr Leu Ala Glu Tyr Met Gly Gln Thr Ser Asp His Glu Ser Gln Val
            100                 105                 110

Thr Phe Thr His Arg Ile Asn Phe Pro Lys Lys Ala Cys Pro Cys Ser
        115                 120                 125

Ser Ser Ala Gln Val Leu Gln Glu Leu Leu Ser Arg Ile Glu Met Leu
    130                 135                 140

Glu Arg Glu Val Ser Val Leu Arg Asp Gln Cys Asn Ala Asn Cys Cys
145                 150                 155                 160

Gln Glu Ser Ala Ala Thr Gly Gln Leu Asp Tyr Ile Pro His Cys Ser
                165                 170                 175

Gly His Gly Asn Phe Ser Phe Glu Ser Cys Gly Cys Ile Cys Asn Glu
            180                 185                 190

Gly Trp Phe Gly Lys Asn Cys Ser Glu Pro Tyr Cys Pro Leu Gly Cys
        195                 200                 205

Ser Ser Arg Gly Val Cys Val Asp Gly Gln Cys Ile Cys Asp Ser Glu
    210                 215                 220

Tyr Ser Gly Asp Asp Cys Ser Glu Leu Arg Cys Pro Thr Asp Cys Ser
```

|     |     |     |     |     |     |     |     |     |     |     |     |     |     |     |     |
| --- | --- | --- | --- | --- | --- | --- | --- | --- | --- | --- | --- | --- | --- | --- | --- |
| 225 |     |     |     |     | 230 |     |     |     |     | 235 |     |     |     |     | 240 |
| Ser | Arg | Gly | Leu | Cys | Val | Asp | Gly | Glu | Cys | Val | Cys | Glu | Glu | Pro | Tyr |
|     |     |     |     | 245 |     |     |     |     | 250 |     |     |     |     | 255 |     |
| Thr | Gly | Glu | Asp | Cys | Arg | Glu | Leu | Arg | Cys | Pro | Gly | Asp | Cys | Ser | Gly |
|     |     |     | 260 |     |     |     |     | 265 |     |     |     |     | 270 |     |     |
| Lys | Gly | Arg | Cys | Ala | Thr | Gly | Thr | Cys | Leu | Cys | Glu | Glu | Gly | Tyr | Val |
|     |     | 275 |     |     |     |     | 280 |     |     |     |     | 285 |     |     |     |
| Gly | Glu | Asp | Cys | Gly | Gln | Arg | Gln | Cys | Leu | Asn | Ala | Cys | Ser | Gly | Arg |
|     | 290 |     |     |     |     | 295 |     |     |     |     | 300 |     |     |     |     |
| Gly | Gln | Cys | Glu | Glu | Gly | Leu | Cys | Val | Cys | Glu | Glu | Gly | Tyr | Gln | Gly |
| 305 |     |     |     |     | 310 |     |     |     |     | 315 |     |     |     |     | 320 |
| Pro | Asp | Cys | Ser | Ala | Val | Ala | Pro | Glu | Asp | Leu | Arg | Val | Ala | Gly |     |
|     |     |     |     | 325 |     |     |     |     | 330 |     |     |     | 335 |     |     |
| Ile | Ser | Asp | Arg | Ser | Ile | Glu | Leu | Glu | Trp | Asp | Gly | Pro | Met | Ala | Val |
|     |     |     | 340 |     |     |     |     | 345 |     |     |     |     | 350 |     |     |
| Thr | Glu | Tyr | Val | Ile | Ser | Tyr | Gln | Pro | Thr | Ala | Leu | Gly | Gly | Leu | Gln |
|     |     | 355 |     |     |     |     | 360 |     |     |     |     | 365 |     |     |     |
| Leu | Gln | Gln | Arg | Val | Pro | Gly | Asp | Trp | Ser | Gly | Val | Thr | Ile | Thr | Glu |
|     | 370 |     |     |     |     | 375 |     |     |     |     | 380 |     |     |     |     |
| Leu | Glu | Pro | Gly | Leu | Thr | Tyr | Asn | Ile | Ser | Val | Tyr | Ala | Val | Ile | Ser |
| 385 |     |     |     |     | 390 |     |     |     |     | 395 |     |     |     |     | 400 |
| Asn | Ile | Leu | Ser | Leu | Pro | Ile | Thr | Ala | Lys | Val | Ala | Thr | His | Leu | Ser |
|     |     |     |     | 405 |     |     |     |     | 410 |     |     |     |     | 415 |     |
| Thr | Pro | Gln | Gly | Leu | Gln | Phe | Lys | Thr | Ile | Thr | Glu | Thr | Thr | Val | Glu |
|     |     |     | 420 |     |     |     |     | 425 |     |     |     |     | 430 |     |     |
| Val | Gln | Trp | Glu | Pro | Phe | Ser | Phe | Ser | Phe | Asp | Gly | Trp | Glu | Ile | Ser |
|     |     | 435 |     |     |     |     | 440 |     |     |     |     | 445 |     |     |     |
| Phe | Ile | Pro | Lys | Asn | Asn | Glu | Gly | Gly | Val | Ile | Ala | Gln | Val | Pro | Ser |
|     | 450 |     |     |     |     | 455 |     |     |     |     | 460 |     |     |     |     |
| Asp | Val | Thr | Ser | Phe | Asn | Gln | Thr | Gly | Leu | Lys | Pro | Gly | Glu | Glu | Tyr |
| 465 |     |     |     |     | 470 |     |     |     |     | 475 |     |     |     |     | 480 |
| Ile | Val | Asn | Val | Val | Ala | Leu | Lys | Glu | Gln | Ala | Arg | Ser | Pro | Pro | Thr |
|     |     |     |     | 485 |     |     |     |     | 490 |     |     |     |     | 495 |     |
| Ser | Ala | Ser | Val | Ser | Thr | Val | Ile | Asp | Gly | Pro | Thr | Gln | Ile | Leu | Val |
|     |     |     | 500 |     |     |     |     | 505 |     |     |     |     | 510 |     |     |
| Arg | Asp | Val | Ser | Asp | Thr | Val | Ala | Phe | Val | Glu | Trp | Ile | Pro | Pro | Arg |
|     |     | 515 |     |     |     |     | 520 |     |     |     |     | 525 |     |     |     |
| Ala | Lys | Val | Asp | Phe | Ile | Leu | Leu | Lys | Tyr | Gly | Leu | Val | Gly | Gly | Glu |
|     | 530 |     |     |     |     | 535 |     |     |     |     | 540 |     |     |     |     |
| Gly | Gly | Arg | Thr | Thr | Phe | Arg | Leu | Gln | Pro | Pro | Leu | Ser | Gln | Tyr | Ser |
| 545 |     |     |     |     | 550 |     |     |     |     | 555 |     |     |     |     | 560 |
| Val | Gln | Ala | Leu | Arg | Pro | Gly | Ser | Arg | Tyr | Glu | Val | Ser | Val | Ser | Ala |
|     |     |     |     | 565 |     |     |     |     | 570 |     |     |     |     | 575 |     |
| Val | Arg | Gly | Thr | Asn | Glu | Ser | Asp | Ser | Ala | Thr | Thr | Gln | Phe | Thr | Thr |
|     |     |     | 580 |     |     |     |     | 585 |     |     |     |     | 590 |     |     |
| Glu | Ile | Asp | Ala | Pro | Lys | Asn | Leu | Arg | Val | Gly | Ser | Arg | Thr | Ala | Thr |
|     |     | 595 |     |     |     |     | 600 |     |     |     |     | 605 |     |     |     |
| Ser | Leu | Asp | Leu | Glu | Trp | Asp | Asn | Ser | Glu | Ala | Glu | Val | Gln | Glu | Tyr |
|     | 610 |     |     |     |     | 615 |     |     |     |     | 620 |     |     |     |     |
| Lys | Val | Val | Tyr | Ser | Thr | Leu | Ala | Gly | Glu | Gln | Tyr | His | Glu | Val | Leu |
| 625 |     |     |     |     | 630 |     |     |     |     | 635 |     |     |     |     | 640 |
| Val | Pro | Lys | Gly | Ile | Gly | Pro | Thr | Thr | Arg | Ala | Thr | Leu | Thr | Asp | Leu |
|     |     |     |     | 645 |     |     |     |     | 650 |     |     |     |     | 655 |     |

```
Val  Pro  Gly  Thr  Glu  Tyr  Gly  Val  Gly  Ile  Ser  Ala  Val  Met  Asn  Ser
               660                 665                      670

Gln  Gln  Ser  Val  Pro  Ala  Thr  Met  Asn  Ala  Arg  Thr  Glu  Leu  Asp  Ser
          675                 680                      685

Pro  Arg  Asp  Leu  Met  Val  Thr  Ala  Ser  Ser  Glu  Thr  Ser  Ile  Ser  Leu
     690                 695                      700

Ile  Trp  Thr  Lys  Ala  Ser  Gly  Pro  Ile  Asp  His  Tyr  Arg  Ile  Thr  Phe
705                      710                 715                           720

Thr  Pro  Ser  Ser  Gly  Ile  Ala  Ser  Glu  Val  Thr  Val  Pro  Lys  Asp  Arg
               725                      730                      735

Thr  Ser  Tyr  Thr  Leu  Thr  Asp  Leu  Glu  Pro  Gly  Ala  Glu  Tyr  Ile  Ile
               740                 745                      750

Ser  Val  Thr  Ala  Glu  Arg  Gly  Arg  Gln  Gln  Ser  Leu  Glu  Ser  Thr  Val
          755                 760                      765

Asp  Ala  Phe  Thr  Gly  Phe  Arg  Pro  Ile  Ser  His  Leu  His  Phe  Ser  His
     770                 775                      780

Val  Thr  Ser  Ser  Ser  Val  Asn  Ile  Thr  Trp  Ser  Asp  Pro  Ser  Pro  Pro
785                 790                      795                           800

Ala  Asp  Arg  Leu  Ile  Leu  Asn  Tyr  Ser  Pro  Arg  Asp  Glu  Glu  Glu  Glu
               805                 810                      815

Met  Met  Glu  Val  Ser  Leu  Asp  Ala  Thr  Lys  Arg  His  Ala  Val  Leu  Met
               820                 825                      830

Gly  Leu  Gln  Pro  Ala  Thr  Glu  Tyr  Ile  Val  Asn  Leu  Val  Ala  Val  His
          835                 840                      845

Gly  Thr  Val  Thr  Ser  Glu  Pro  Ile  Val  Gly  Ser  Ile  Thr  Thr  Gly  Ile
     850                 855                      860

Asp  Pro  Pro  Lys  Asp  Ile  Thr  Ile  Ser  Asn  Val  Thr  Lys  Asp  Ser  Val
865                      870                 875                           880

Met  Val  Ser  Trp  Ser  Pro  Pro  Val  Ala  Ser  Phe  Asp  Tyr  Tyr  Arg  Val
               885                 890                      895

Ser  Tyr  Arg  Pro  Thr  Gln  Val  Gly  Arg  Leu  Asp  Ser  Ser  Val  Val  Pro
               900                 905                      910

Asn  Thr  Val  Thr  Glu  Phe  Thr  Ile  Thr  Arg  Leu  Asn  Pro  Ala  Thr  Glu
          915                 920                      925

Tyr  Glu  Ile  Ser  Leu  Asn  Ser  Val  Arg  Gly  Arg  Glu  Glu  Ser  Glu  Arg
     930                 935                      940

Ile  Cys  Thr  Leu  Val  His  Thr  Ala  Met  Asp  Asn  Pro  Val  Asp  Leu  Ile
945                      950                 955                           960

Ala  Thr  Asn  Ile  Thr  Pro  Thr  Glu  Ala  Leu  Leu  Gln  Trp  Lys  Ala  Pro
               965                 970                      975

Val  Gly  Glu  Val  Glu  Asn  Tyr  Val  Ile  Val  Leu  Thr  His  Phe  Ala  Val
          980                 985                      990

Ala  Gly  Glu  Thr  Ile  Leu  Val  Asp  Gly  Val  Ser  Glu  Glu  Phe  Arg  Leu
          995                 1000                     1005

Val  Asp  Leu  Leu  Pro  Ser  Thr  His  Tyr  Thr  Ala  Thr  Met  Tyr  Ala  Thr
     1010                1015                     1020

Asn  Gly  Pro  Leu  Thr  Ser  Gly  Thr  Ile  Ser  Thr  Asn  Phe  Ser  Thr  Leu
1025                     1030                1035                          1040

Leu  Asp  Pro  Pro  Ala  Asn  Leu  Thr  Ala  Ser  Glu  Val  Thr  Arg  Gln  Ser
               1045                1050                     1055

Ala  Leu  Ile  Ser  Trp  Gln  Pro  Pro  Arg  Ala  Glu  Ile  Glu  Asn  Tyr  Val
               1060                1065                     1070

Leu  Thr  Tyr  Lys  Ser  Thr  Asp  Gly  Ser  Arg  Lys  Glu  Leu  Ile  Val  Asp
               1075                1080                     1085
```

Ala Glu Asp Thr Trp Ile Arg Leu Glu Gly Leu Leu Glu Asn Thr Asp
    1090            1095            1100

Tyr Thr Val Leu Leu Gln Ala Thr Gln Asp Thr Thr Trp Ser Ser Ile
1105            1110            1115            1120

Thr Ser Thr Ala Phe Thr Thr Gly Gly Arg Val Phe Pro His Pro Gln
            1125            1130            1135

Asp Cys Ala Gln His Leu Met Asn Gly Asp Thr Leu Ser Gly Val Tyr
            1140            1145            1150

Pro Ile Phe Leu Asn Gly Glu Leu Ser Gln Lys Leu Gln Val Tyr Cys
        1155            1160            1165

Asp Met Thr Thr Asp Gly Gly Gly Trp Ile Val Phe Gln Arg Arg Gln
    1170            1175            1180

Asn Gly Gln Thr Asp Phe Phe Arg Lys Trp Ala Asp Tyr Arg Val Gly
1185            1190            1195            1200

Phe Gly Asn Val Glu Asp Glu Phe Trp Leu Gly Leu Asp Asn Ile His
            1205            1210            1215

Arg Ile Thr Ser Gln Gly Arg Tyr Glu Leu Arg Val Asp Met Arg Asp
            1220            1225            1230

Gly Gln Glu Ala Ala Phe Ala Ser Tyr Asp Arg Phe Ser Val Glu Asp
        1235            1240            1245

Ser Arg Asn Leu Tyr Lys Leu Arg Ile Gly Ser Tyr Asn Gly Thr Ala
    1250            1255            1260

Gly Asp Ser Leu Ser Tyr His Gln Gly Arg Pro Phe Ser Thr Glu Asp
1265            1270            1275            1280

Arg Asp Asn Asp Val Ala Val Thr Asn Cys Ala Met Ser Tyr Lys Gly
            1285            1290            1295

Ala Trp Trp Tyr Lys Asn Cys His Arg Thr Asn Leu Asn Gly Lys Tyr
            1300            1305            1310

Gly Glu Ser Arg His Ser Gln Gly Ile Asn Trp Tyr His Trp Lys Gly
            1315            1320            1325

His Glu Phe Ser Ile Pro Phe Val Glu Met Lys Met Arg Pro Tyr Asn
    1330            1335            1340

His Arg Leu Met Ala Gly Arg Lys Arg Gln Ser Leu Gln Phe
1345            1350            1355